United States Patent [19]

Nease et al.

[11] Patent Number: 5,705,013

[45] Date of Patent: *Jan. 6, 1998

[54] METHOD FOR MANUFACTURING EXTENSIBLE SIDE PANELS FOR ABSORBENT ARTICLES

[75] Inventors: Michael G. Nease, Fairfield; Bradley E. Walsh; Robert E. Askin, both of Cincinnati, all of Ohio; Joseph A. Eckstein, Sunman, Ind.

[73] Assignee: The Procter & Gamble Company, Cincinnati, Ohio

[*] Notice: The term of this patent shall not extend beyond the expiration date of Pat. No. 5,580,411.

[21] Appl. No.: 662,400

[22] Filed: Jun. 12, 1996

Related U.S. Application Data

[63] Continuation-in-part of Ser. No. 386,832, Feb. 10, 1995, Pat. No. 5,580,411.

[51] Int. Cl.$^6$ .................. A61F 13/56; B32B 31/12
[52] U.S. Cl. .................. 156/260; 156/163; 156/264; 156/265; 604/385.1
[58] Field of Search .................. 156/260, 163, 156/264, 265, 259, 266, 256, 263, 66, 182, 512, 177, 160, 199, 200, 204, 221, 269, 270; 604/385.1, 385.2, 384, 390, 389

[56] References Cited

U.S. PATENT DOCUMENTS

| | | | |
|---|---|---|---|
| 1,424,005 | 7/1922 | Drury . | |
| 1,776,353 | 9/1930 | Dunbar et al. . | |
| 2,709,475 | 5/1955 | Steckel et al. | 154/1 |
| 3,072,123 | 1/1963 | Davis | 128/284 |
| 3,180,335 | 4/1965 | Duncan et al. | 128/287 |
| 3,488,778 | 1/1970 | Goujon et al. | 2/224 |
| 3,527,221 | 9/1970 | Croon | 128/287 |
| 3,559,648 | 2/1971 | Mason, Jr. | 128/287 |
| 3,566,752 | 3/1971 | Dreher | 93/1 |
| 3,623,927 | 11/1971 | Watson | 156/177 |
| 3,636,951 | 1/1972 | Glasgow | 128/284 |
| 3,691,570 | 9/1972 | Gaines et al. | 5/347 |
| 3,699,966 | 10/1972 | Chapuis | 128/290 R |
| 3,744,383 | 7/1973 | Finch et al. | 93/35 R |
| 3,744,494 | 7/1973 | Marsan | 128/287 |
| 3,768,530 | 10/1973 | Coco | 144/318 |
| 3,776,233 | 12/1973 | Schaar | 128/287 |
| 3,860,003 | 1/1975 | Buell | 128/287 |

(List continued on next page.)

FOREIGN PATENT DOCUMENTS

| | | | |
|---|---|---|---|
| 0233704 | 8/1987 | European Pat. Off. | A61F 5/44 |
| 0528282 | 2/1993 | European Pat. Off. | A61F 13/15 |
| 0539032 | 4/1993 | European Pat. Off. | A61F 13/15 |
| 2644694 | 9/1990 | France | A61F 13/46 |
| 2160103 | 12/1985 | United Kingdom | A61F 13/00 |
| 2161059 | 1/1988 | United Kingdom | A41B 13/02 |
| 2196834 | 5/1988 | United Kingdom | A41B 13/02 |
| 2197181 | 5/1988 | United Kingdom | A41B 13/02 |

Primary Examiner—David A. Simmons
Assistant Examiner—Linda L. Gray
Attorney, Agent, or Firm—David M. Weirich; Steven W. Miller; Jacobus C. Rasser

[57] ABSTRACT

A zero scrap method for manufacturing side panels for use with absorbent articles including the following steps. First, a web of material having predetermined portions is provided in a machine direction. The predetermined portions are then activated to provide stretch in the side panels. The web is then cut continuously severing the web into a first panel and a second panel, each of the panels having alternating, nested inwardly extending elements defined by the cut and terminating at a distal edge. The inwardly extending elements are offset with respect to each other in the machine direction. The first and second panels are separated and positioned such that the inwardly extending elements of the first panel and the inwardly extending elements of the second panel are aligned in the machine direction. The distal edge of the inwardly extending elements of at least a portion of the first panel is then joined with at least a portion of the distal edge of the inwardly extending elements of the second panel. Finally, the composite of the first and second panels is severed in the cross machine direction to create an extensible side panel that can be joined to an absorbent article.

16 Claims, 8 Drawing Sheets

U.S. PATENT DOCUMENTS

| | | | |
|---|---|---|---|
| 3,871,378 | 3/1975 | Duncan et al. | 128/290 |
| 3,875,837 | 4/1975 | Dussaud | 83/46 |
| 3,878,283 | 4/1975 | Jones, Sr. | 264/152 |
| 3,890,973 | 6/1975 | Davis et al. | 128/286 |
| 3,929,134 | 12/1975 | Karami | 128/284 |
| 4,029,101 | 6/1977 | Chesky et al. | 128/290 R |
| 4,040,423 | 8/1977 | Jones, Sr. | 128/287 |
| 4,041,950 | 8/1977 | Jones, Sr. | 128/287 |
| 4,210,143 | 7/1980 | De Jonckheere | 128/287 |
| 4,259,958 | 4/1981 | Goodbar | 128/287 |
| 4,325,372 | 4/1982 | Teed | 128/287 |
| 4,381,782 | 5/1983 | Mazurak et al. | 604/368 |
| 4,425,127 | 1/1984 | Suzuki et al. | 604/366 |
| 4,439,260 | 3/1984 | Canterino et al. | 156/259 |
| 4,490,148 | 12/1984 | Beckestrom | 604/385 |
| 4,500,316 | 2/1985 | Damico | 604/389 |
| 4,518,451 | 5/1985 | Luceri et al. | 156/202 |
| 4,557,777 | 12/1985 | Sabee | 156/201 |
| 4,595,441 | 6/1986 | Holvoet et al. | 156/265 |
| 4,610,751 | 9/1986 | Eschler | 156/517 |
| 4,666,550 | 5/1987 | Spiers et al. | 156/361 |
| 4,670,011 | 6/1987 | Mesek | 604/378 |
| 4,670,960 | 6/1987 | Provost | 29/415 |
| 4,690,719 | 9/1987 | Lucas et al. | 156/201 |
| 4,704,115 | 11/1987 | Buell | 604/385 A |
| 4,729,814 | 3/1988 | Jennus et al. | 156/512 |
| 4,731,071 | 3/1988 | Pigneul | 604/385 R |
| 4,753,645 | 6/1988 | Johnson | 604/378 |
| 4,756,958 | 7/1988 | Bryant et al. | 428/320.2 |
| 4,760,764 | 8/1988 | De Jonckheere et al. | 83/23 |
| 4,781,710 | 11/1988 | Megison et al. | 604/378 |
| 4,787,896 | 11/1988 | Houghton et al. | 604/385.1 |
| 4,795,453 | 1/1989 | Wolfe | 604/385.1 |
| 4,822,435 | 4/1989 | Igaue et al. | 156/164 |
| 4,834,740 | 5/1989 | Suzuki et al. | 604/385.2 |
| 4,862,574 | 9/1989 | Seidy | 29/415 |
| 4,869,942 | 9/1989 | Jennus et al. | 428/77 |
| 4,900,317 | 2/1990 | Buell | 604/370 |
| 4,917,750 | 4/1990 | Klose | 156/254 |
| 4,938,753 | 7/1990 | Van Gompel et al. | 604/385.2 |
| 4,940,464 | 7/1990 | Van Gompel et al. | 604/396 |
| 4,950,355 | 8/1990 | Klose | 156/204 |
| 4,960,477 | 10/1990 | Mesek | 156/209 |
| 4,994,052 | 2/1991 | Kimura | 604/355 |
| 5,007,906 | 4/1991 | Osborn, III et al. | 604/385.1 |
| 5,021,051 | 6/1991 | Hiuke | 604/385.2 |
| 5,034,007 | 7/1991 | Igaue et al. | 604/365 |
| 5,064,489 | 11/1991 | Ujimoto et al. | 156/164 |
| 5,080,741 | 1/1992 | Nomura et al. | 156/201 |
| 5,102,487 | 4/1992 | Lamb | 156/260 |
| 5,110,386 | 5/1992 | Ochi et al. | 156/204 |
| 5,123,316 | 6/1992 | Niedermaier et al. | 83/29 |
| 5,134,007 | 7/1992 | Reising et al. | 428/78 |
| 5,151,091 | 9/1992 | Glaug et al. | 604/385.1 |
| 5,156,793 | 10/1992 | Buell et al. | 264/288.8 |
| 5,165,979 | 11/1992 | Watkins et al. | 428/113 |
| 5,167,897 | 12/1992 | Weber et al. | 264/288.8 |
| 5,295,988 | 3/1994 | Muckenfuhs et al. | 604/385.2 |
| 5,300,054 | 4/1994 | Feist et al. | 604/378 |
| 5,354,400 | 10/1994 | Lavash et al. | 156/227 |
| 5,399,219 | 3/1995 | Roessler et al. | 156/259 |
| 5,580,411 | 12/1996 | Nease et al. | 156/260 |

METHOD FOR MANUFACTURING EXTENSIBLE SIDE PANELS FOR ABSORBENT ARTICLES

This application is a continuation-in-part of application Ser. No. 08/386,832, filed on Feb. 10, 1995, now U.S. Pat. No. 5,580,411.

FIELD OF THE INVENTION

This invention relates to a method for manufacturing side panels for absorbent articles, and more particularly to a zero scrap method of manufacturing elastically extensible side panels for absorbent articles.

BACKGROUND OF THE INVENTION

Disposable absorbent articles such as diapers, training pants, incontinence garments, feminine hygiene garments and the like have become very popular in the market place today. Many of these articles include features such as side panels that provide a variety of functions including improved containment characteristics and better, more comfortable fit.

An overriding consideration in the construction of a disposable absorbent article is the cost of manufacturing the article, including the materials cost. The present invention provides methods for manufacturing side panels for absorbent articles with little or no wasted material. Thus, the side panels made by the process of the present invention can be provided at a relatively lower cost than many of the side panels that are current manufacturing using techniques in which material is wasted. Accordingly, the method of the present invention can reduce the overall cost of the absorbent article.

Therefore, it is an object of the present invention to provide a method for manufacturing side panels for absorbent articles with little or no waste.

It is a further object of the present invention to provide a method for manufacturing relatively low cost side panels for absorbent articles.

It is yet a further object of the present invention to provide a method for manufacturing "zero scrap", low cost, elastically extensible side panels for use with absorbent articles.

It is still a further object of the present invention to provide a method for manufacturing little or no scrap, multi-directional side panel for use with absorbent articles.

It is still a further object of the present invention to provide a method for manufacturing little or no scrap multi-piece, multi-directional side panels for use with absorbent articles.

SUMMARY OF THE INVENTION

The present invention provides a zero scrap method for manufacturing side panels for use with absorbent articles. In one preferred embodiment, the present invention provides a zero scrap method for manufacturing multi-directional extensible side panels including the following steps. First, a web of material having predetermined portions is provided in a machine direction. The predetermined portions are then activated to provide stretch in the side panels. The web is then cut by continuously severing the web into a first panel and a second panel, each of the panels having alternating, nested inwardly extending elements defined by the cut and terminating at a distal edge. The inwardly extending elements are offset with respect to each other in the machine direction. The first and second panels are separated and positioned such that the inwardly extending elements of the first panel and the inwardly extending elements of the second panel are aligned in the machine direction. After the inwardly extending elements are in alignment, the distal edge of at least a portion of the first panel is joined with at least a portion of the distal edge of the second panel. Finally, the composite of the first and second panels is cut in the cross machine direction such that every two cuts define a pair of multi-directional, extensible side panels that can be joined to an absorbent article.

BRIEF DESCRIPTION OF THE DRAWINGS

While the specification concludes with claims particularly pointing out and distinctly claiming the subject matter which is regarded as the present invention, it is believed that the invention will be better understood from the following description taken in conjunction with the accompanying drawings, in which:

DETAILED DESCRIPTION OF THE INVENTION

The zero scrap method of the present invention is particularly suited for manufacturing side panels for use with disposable absorbent articles. As used herein, the term "zero scrap" refers to a method of manufacturing side panels that produces little or no scrap material. The term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use (i.e. they are intended to be discarded, and preferably, recycled, composted or otherwise disposed of in an environmentally compatible manner). A "unitary" absorbent article refers to an absorbent article which is formed from separate parts united together to form a coordinated entity so that they do not require separate manipulative parts like a separate holder and liner. A preferred embodiment of a unitary absorbent article comprising tape tabs manufactured by the method of the present invention is the disposable absorbent article shown in FIG. 1. As used herein, the term "diaper" refers to an absorbent article generally worn by infants and incontinent persons that is generally worn about the lower torso of the wearer. It should be understood, however, that the present invention is also applicable to other absorbent articles such as incontinence briefs, diaper holders, feminine hygiene garments, training pants, and the like.

Figure 1:
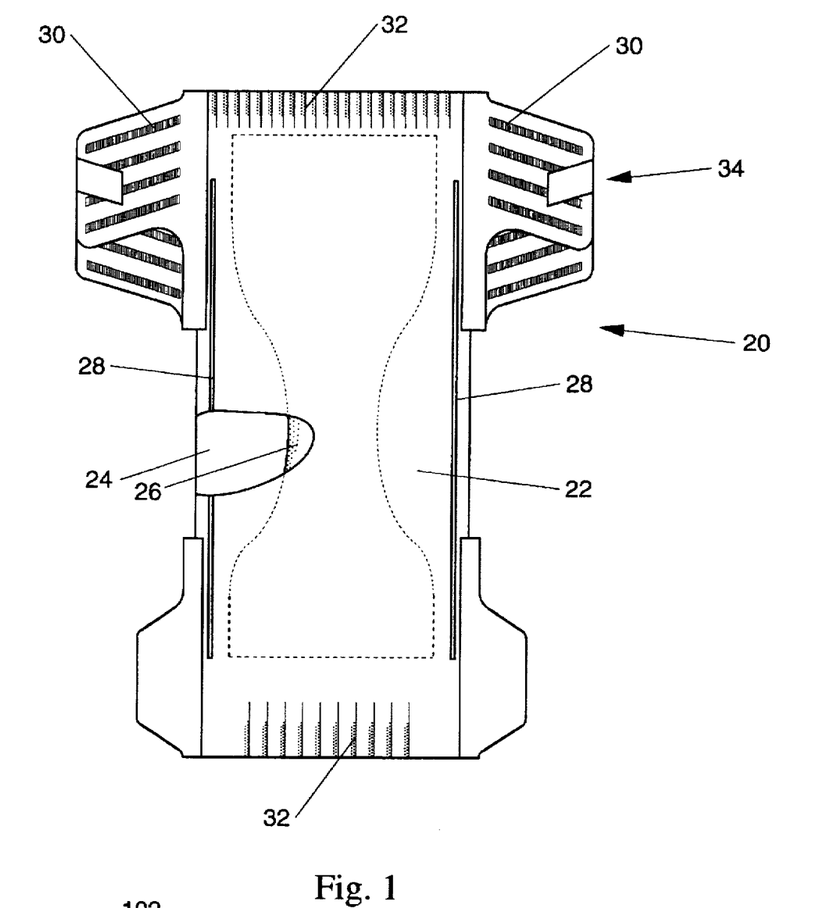
FIG. 1 is a plan view of an absorbent article comprising side panels manufactured in accordance with the method of the present invention.

With reference to FIG. 1, an absorbent article, such as diaper 20, generally comprises a liquid permeable topsheet 22, a liquid impermeable backsheet 24, and an absorbent core 26 sandwiched between the topsheet 22 and the backsheet 24. The diaper 20 preferably further comprises elasticized leg cuffs 28, side panels 30, an elastic waist feature 32 and a fastening system 34. An example of an absorbent article to which the side panels 30 of the present invention may be joined is more fully and completely described in the commonly assigned, copending U.S. patent application Ser. No. 08/155,048 entitled "Absorbent Article with Multi-directional Extensible Side Panels", filed on Nov. 19, 1993 in the names of Robles, et al., which is hereby incorporated by reference herein.

Method for Manufacturing Side Panels

Figure 2:
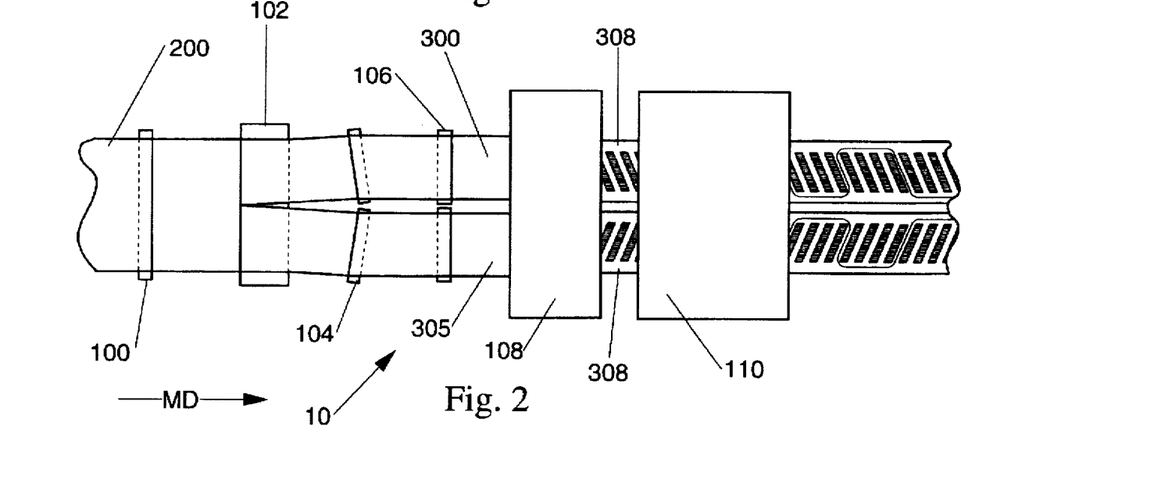
FIG. 2 is schematic plan view of a portion of the side panel making process including the activation and die cutting steps.
Figure 3:
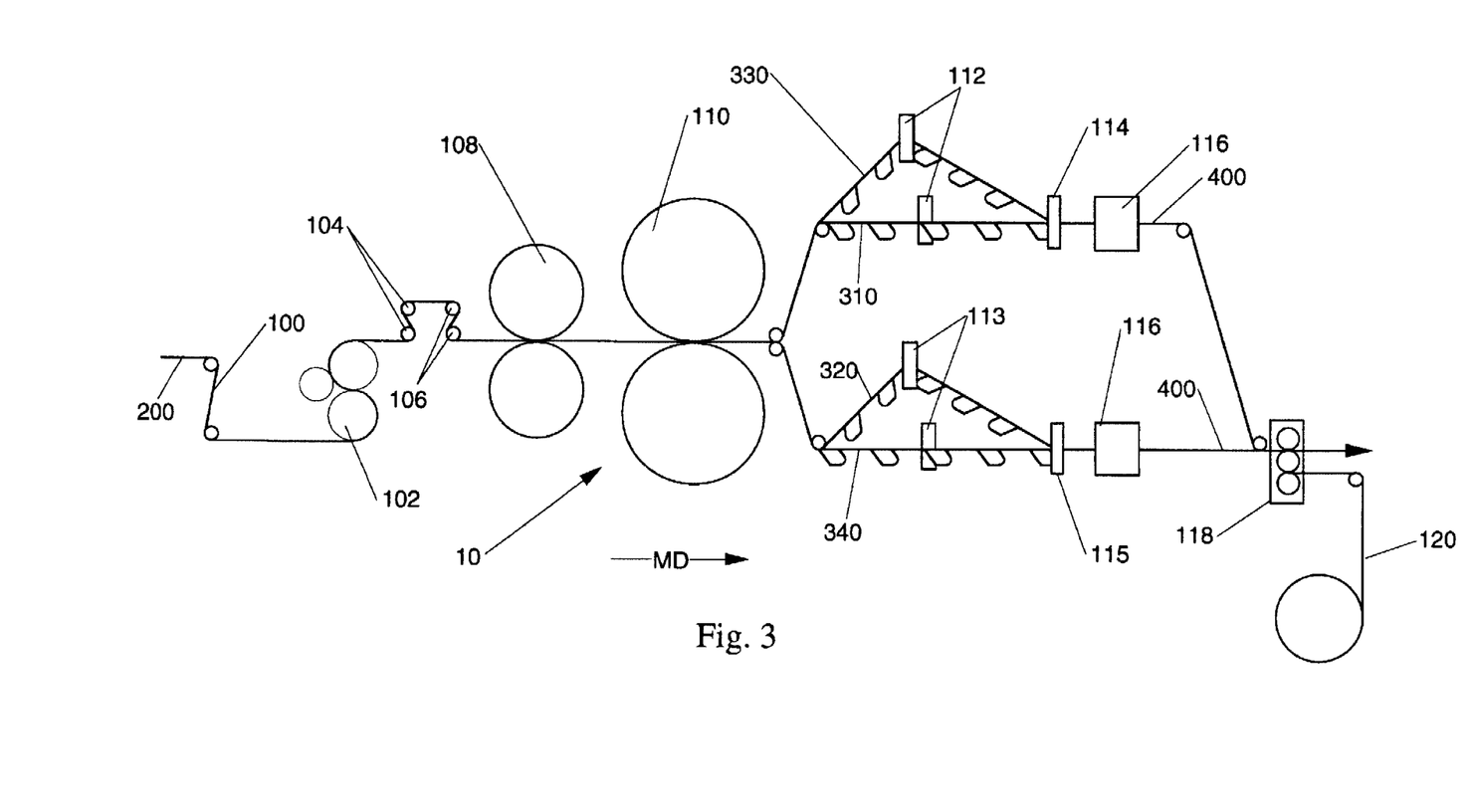
FIG. 3 is a schematic side view of the process of the present invention.

The side panels 30 may be produced on the apparatus 10 shown in FIGS. 2 and 3. In a preferred embodiment, the apparatus 10 is integrated into a disposable absorbent article manufacturing line such that the side panels 30 may be manufactured "on-line". (As used herein, the term "integrated" refers to interconnected process modules that operate concurrently to produce finished products from source materials. The term "on-line" is used to refer to the process of manufacturing the side panels 30 on an apparatus that is integrated with the manufacturing line that produces the disposable absorbent articles to which the side panels 30 will be joined.)

Examining the process in greater detail, the material from which the side panels are made is first provided to the apparatus 10. The material may be made "on-line" in a process preceding the process for manufacturing the side panels 36, or the material may be produced off-line and brought to the side panel manufacturing apparatus 10. Despite the origin or process used to make the material from which the side panels 30 are produced, the material preferably comprises a laminate of more than one stock material (However, it should be noted that the side panels 30 may be produced from a single stock material.) In a preferred embodiment, the material comprises a laminate of polyethylene film as an outer cover stock, a filler material and a nonwoven material as the inner cover stock. The materials are preferably combined together with a spiral coating of FINDLEY 2085 adhesive; however, any other suitable adhesive or means of joining the materials known in the art may be used. One example of a suitable outer cover stock material is available from the CLOPAY Corporation of Cincinnati, Ohio under the trade designation Clopay 1401.

Materials from which suitable outer cover stock may be made include, but are not limited to polyolefins such as polyethylenes, including linear low density polyethylene, low density polyethylene, ultra low density polyethylene, high density polyethylene, polypropylene, polyester, polyurethane, compostable or biodegradable polymers, heat shrink polymers, thermoplastic polymers, metallocene catalyst based polymers (e.g., INSITE available from Dow Chemical Company, EXXACT available from Exxon and CPC2 polyethylene available from Tredegar, Inc.).

Suitable filler materials include, but are not limited to the apertured formed fills available from Tredegar Film Products, Inc. of Terre Haute, Ind., two-dimensional apertured films, macroscopically expanded, three-dimensional apertured formed films, polymer films, nonwovens, foams, thermally bonded air-laid fibrous structures and composites or laminates of any of the above. Other filler materials are described in U.S. Pat. No. 4,342,314 issued to Radel, et al.; U.S. Pat. No. 4,463,045 issued to Ahr, et al.; U.S. Pat. No. 3,929,135 issued to Thompson; U.S. Pat. No. 4,324,246 issued to Mullane, et al.; and U.S. Pat. No. 5,006,394 issued to Baird. Each of these patents are incorporated by reference herein.

An acceptable nonwoven can be obtained from Fiberweb North America, Inc. of Greenville, S.C. under the trade designation P-14. However, other suitable nonwovens include, but are not limited to those comprising natural fibers such as cotton or wool; synthetic fibers of nylon, polyamides, polyesters, or polyolefins; yarns; polyethylene; polypropylene or any combination of these or other materials known in the art. The nonwoven webs may be manufactured in any of the following ways: spunlace, spunbond, meltblown, carded, air-through, calender bonded or any other method that is known in the art.

Once the side panel laminate 200 is formed and brought to the side panel manufacturing apparatus 10, the laminate 200 is preferably "unwound" and fed into the side panel manufacturing apparatus 10. (As used herein, the term "unwound" means to remove the laminate 200 from a roll, a box or other device on which it is transported to the site of the manufacturing apparatus 10 or stored before being fed into the manufacturing process.) The laminate 200 may be unwound by any unwind system (not shown) as is known in the art. In a preferred embodiment the unwind system comprises a tensioning device (not shown) and a metering device (not shown). Accordingly, the laminate 200 is first put under tension by means of a standard tensioning device, commonly known in the art as a dancer. The tensioning device provides tracking capabilities so that the laminate 200 may be properly fed into the metering device. The metering device, such as a powered roll or S wrap, feeds the laminate 200 into side panel manufacturing apparatus 10 at a constant speed. Suitable unwind systems are available from the Curt Joa Corporation of Sheboygan Falls, Wis. and from the Machintek Corporation of Fairfield, Ohio.

After the laminate 200 is fed into the process, it is preferably passes through a tracking device 100, as is commonly known in the art, to center the laminate 200. A tracking device manufactured by the Fife Corporation of Oklahoma City, Okla. under the trade designation FIFE A9 is an example of a suitable tracking device 100.

The laminate 200 is then preferably cut with a standard industry slitting device 102 to create two web portions 300 and 305 of generally equal width, each of the webs having two longitudinal side edges 250. (However, it should be understood that the laminate 200 may be cut into any number of webs or may remain a single web that is processed as described below. Further, the two web portions 300 and 305 could be individual webs that are separately fed into the process as described above.) The two web portions 300 and 305 are then separated by any means as are known in the art. In a preferred embodiment, as shown in FIG. 2, the web portions 300 and 305 are separated by canted or angled idlers 104. The two web portions 300 and 305 then pass through a second tracking system 106 to center the webs before the activation and die cutting steps of the process. An exemplary tracking system 106 comprises a tracking device available from the Fife Corporation under the trade designation FIFE Symat 25.

As shown in FIG. 2, after the laminate 200 is cut and separated the individual web portions 300 and 305 are activated by the activation unit 108. (However, it should be understood that the activation step may precede the step in which the laminate 200 is cut as described above.) As used herein, the term "activated" means to mechanically deform a material so as to impart elasticity in the material such that the material may elastically extend in one or more directions. "Elastically extensible" materials extend in at least one direction when a force is applied and return to approximately their original dimensions after the force is removed. The web portions 300 and 305 may be activated by any means as are known in the art, including, but not limited to ring rolling, embossing, thermoforming, high pressure hydraulic forming or casting. These means for providing elasticity to the web portions 300 and 305 and other means not mentioned obviate the need for additional elastomeric materials and thus, are generally preferred over methods necessitating the addition of elastomeric material or materials. However, embodiments of the present invention are contemplated wherein additional elastomeric materials such as elastic, natural or synthetic rubber, rubber foams, elastomeric scrims, woven or nonwoven elastomeric webs, elastomeric composites, zero-strain stretch laminates, prestrained stretch laminates or the like are used to provide elasticity to the webs. Some examples of preferred methods for imparting elasticity to the web portions 300 and 305 are described in detail in U.S. Pat. No. 5,156,793 entitled "Method for Incrementally Stretching Zero Strain Stretch Laminate Web in a Non-uniform Manner to Impart a Varying Degree of Elasticity Thereto", issued to Buell et al., on Oct. 20, 1992; U.S. Pat. No. 5,167,897 entitled "Method for Incrementally Stretching a Zero Strain Stretch Laminate Web to Impart Elasticity Thereto", issued to Weber et al., on Dec. 1, 1992; and co-pending U.S. patent application Ser. No. 08/203,087 entitled "Web Materials Exhibiting Elastic-Like Behavior", filed in the names of Chappell et al., on Feb. 28, 1994. Each of the above-identified U.S. patents and the U.S. patent application are hereby incorporated by reference herein.

Figure 4:
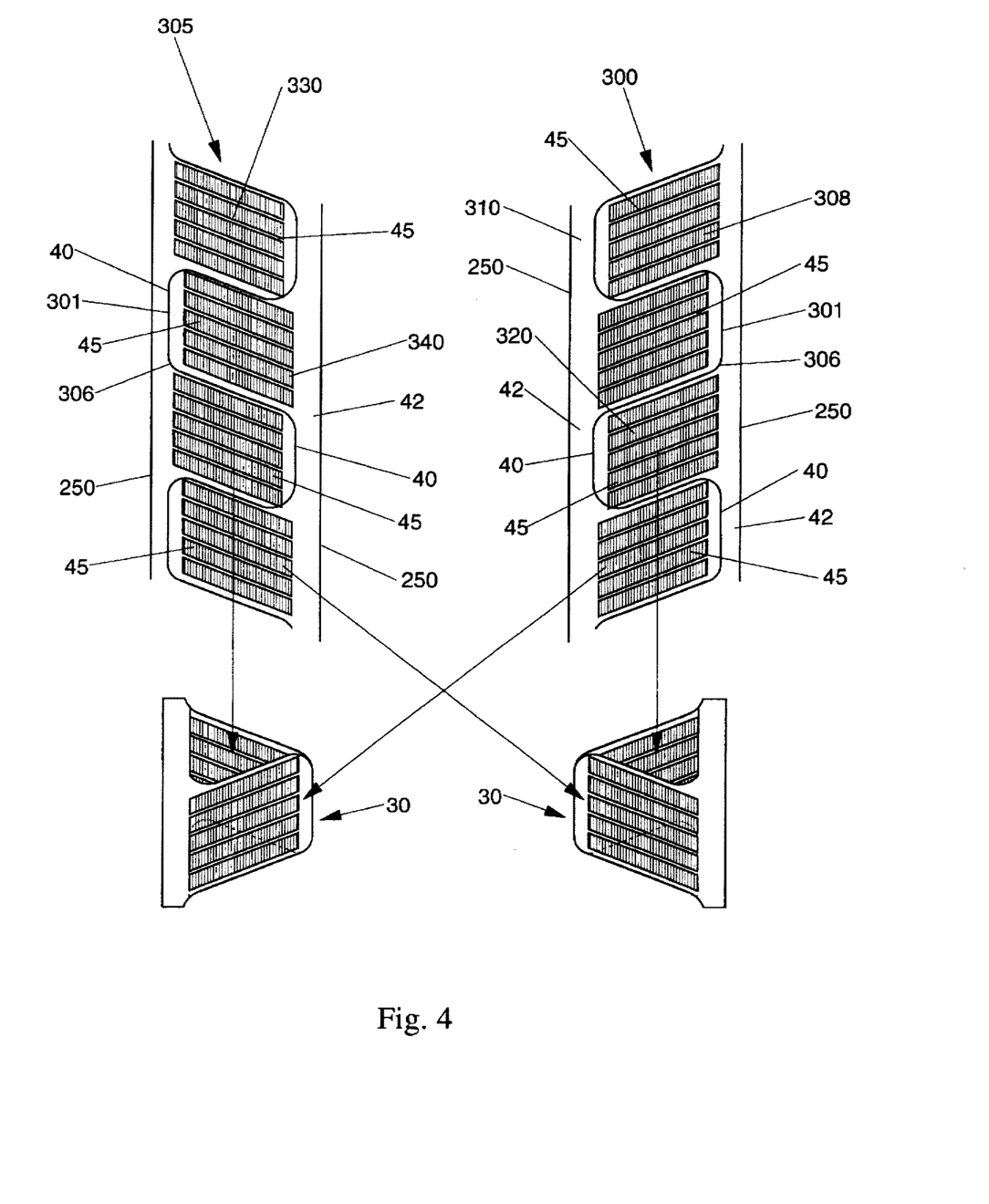
FIG. 4 is an illustration of one embodiment of the side panels provided by the present invention showing a preferred configuration in which portions of the web material are combined to form multi-directional, extensible side panels.
Figure 6:
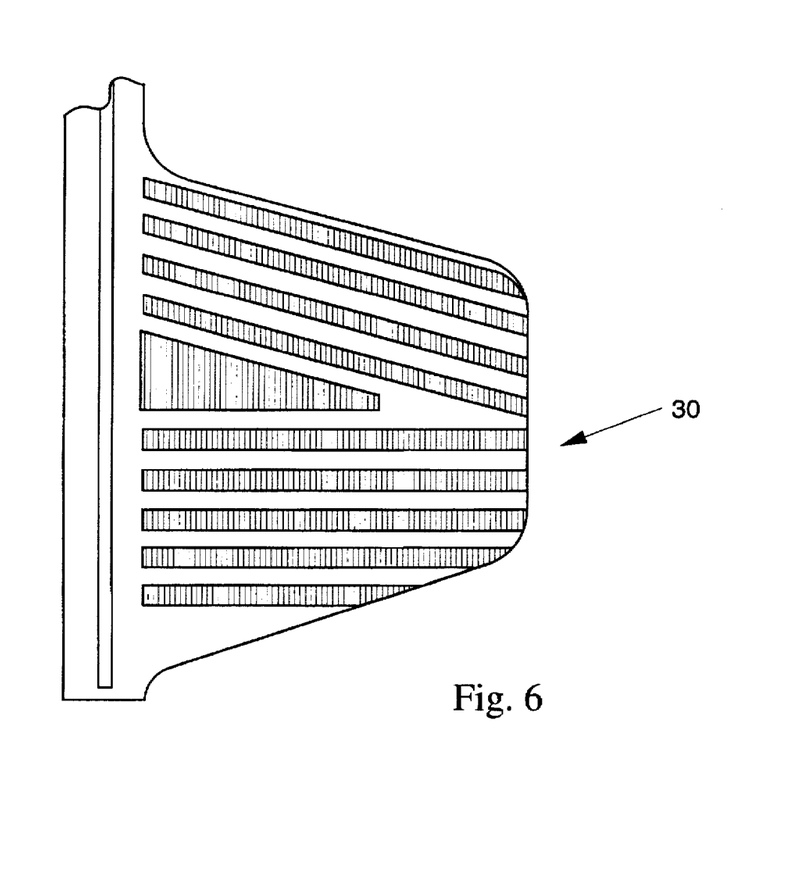
FIG. 6 is an illustration of a side panel manufactured by an alternative embodiment of the process of the present invention.
Figure 7:
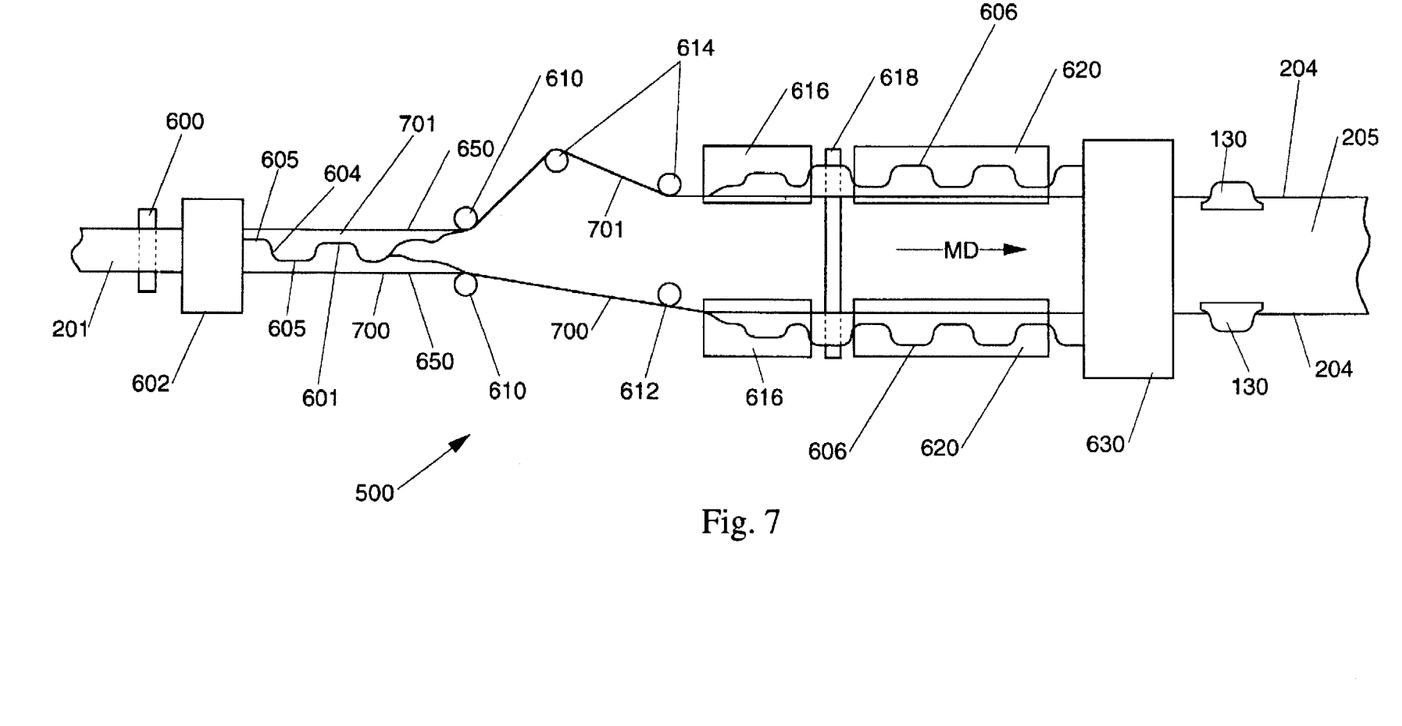
FIG. 7 is a schematic plan view of a portion of an alternative side panel making process.

A preferred pattern of activation 308 is shown in FIG. 2, and more clearly in FIG. 4. The pattern 308 gives the side panels 30 multi-directional stretch characteristics when the side panels 30 are constructed according to the method steps that follow. Further, the pattern 308 shown in FIG. 4 is preferably phased in both the machine direction and the cross machine direction to correspond with the die cut pattern 306. (As used herein, the term "machine direction" refers to the general direction in which the materials being processed move. The machine direction is shown in FIGS. 2, 3 and 7 by the arrow MD. The term "cross machine direction" is the direction generally perpendicular to the machine direction. As used herein, the terms "phased" or "in phase" means that the die cut pattern 306 is controlled in such a way that it is continuously repeated such that it coincides with predetermined portions of the web or the activation pattern 308.) Other patterns of activation 308 are contemplated, including, but not limited to uniform patterns wherein the pattern of activation 308 is generally the same throughout the entire web or nonuniform patterns wherein the pattern of activation 308 may comprise several different regions of activation that provide the web or portions of the web with different mounts or directions of elasticity. Further, the area of activation may vary depending on the stretch characteristics desired. (An example of a side panel comprising varying patterns of activation is illustrated in FIG. 6.)

Once the web portions 300 and 305 are activated, each of the web portions 300 and 305 is preferably cut into two distinct panels. Thus, at this point, the laminate 200 preferably has been cut into four pieces; web portion 300 is cut into first panel 310 and second panel 320, and web portion 305 is cut into third panel 330 and fourth panel 340 (shown in FIG. 4). The web portions 300 and 305 may be cut in symmetrical patterns or may be cut in patterns that are different from each other. (Web portions 300 and 305 are shown cut in a preferred symmetrical pattern in FIG. 4.)

In a preferred embodiment of the present invention, the web portions 300 and 305 are die cut by the die cutting assembly 110. The die cutting assembly 110 may be any die cutting assembly as is known in the art, however, in a preferred embodiment, the die cutting assembly 110 comprises anvil rolls having vacuum holes that hold the web portions 300 and 305 in place while they are cut. Further, it is preferred that the die cutting assembly 110 be close coupled or driven from the same drive as the activation unit 108 so that the die cut pattern 306 can be maintained in phase with the activation pattern 308.

The die cut pattern 306 on each of the web portions 300 and 305 is preferably a continuous cut made as the web portions 300 and 305 move in the machine direction. (The term "continuous" as used herein means generally unending or without interruption. However, the term is not to be construed so as to exclude a series of slits or perforations that provide adequate separation of the webs.) The die cut pattern 306 preferably comprises portions that are generally parallel to the machine direction alternating with portions that are generally perpendicular to the machine direction. (As used herein, the term "generally parallel" refers to lines of direction that are parallel to or at an angle of less than 45 degrees from the direction from which the line of direction is being measured. The term "generally perpendicular" refers to lines of direction that are perpendicular to or at an angle of more than 45 degrees from the direction from which the line of direction is being measured.) Thus, the die cut pattern 306 repeatedly cuts at least partially across the web portions 300 and 305 as the webs move in the machine direction. Although the die cut pattern 306 may take on any number of patterns, in preferred embodiments the die cut pattern 306 is configured such that little or no scrap is produced during the method of manufacturing the side panels 30. Further, for handling and other purposes it is preferred that the cut does not reach the longitudinal side edges 250 of the webs. (A particularly preferred die cut pattern 306 is illustrated in FIG. 4.)

Each die cut 301 preferably severs one of the web portions 300 and 305 into a pair of distinct panels. As shown in FIG. 4, web portion 300 is cut into complementary panels, first panel 310 and second panel 320 while web portion 305 is cut into complementary panels, third panel 330 and fourth panel 340. (As used herein, the term "complementary panels" refers to a pair of panels that are cut from a single web, such as first panel 310 and second panel 320 shown in FIG. 4.) Each panel has inwardly extending elements 45 that extend inwardly from one of the longitudinal edges 250 of the panel. The inwardly extending elements 45 are defined by the cut 301 and terminate at a distal edge 40. The distal edges 40 of the inwardly extending elements 45 are adjacent to the proximal portions 42 of the complementary panel. The proximal portions 42 are those portions of the panels that are located between the longitudinal side edges 250 and the distal edges 40; the proximal portions 42 being separated from the distal edges 40 by the cut 301. The inwardly extending elements 45 of each pair of complementary panels are preferably offset in the machine direction from one another such that the inwardly extending elements 45 of the panels alternate with each other, and thus are in a nested configuration as shown in FIG. 4. This alternating nested configuration provides for little or no wasted material as the complementary panels are further machined into their final form as multi-piece, multi-directional side panels 30.

Upon exiting the die cutting assembly 110, the complementary panels are separated from each other such that the individual panels, first panel 310 and third panel 330 are apart from their complementary panels second panel 320 and fourth 340, respectively. The separation of the complementary panels may be performed by any method known in the art. In a preferred embodiment, as shown in FIG. 3, first panel 310 and third panel 330 are directed to one assembly of idlers 112 which serves to rotate, align and phase the panels 310 and 330 before they are joined as described in more detail below. Likewise, second panel 320 and fourth panel 340 are directed to an assembly of idlers 113 which serves to rotate, align and phase panels 320 and 340 before they are joined. (It has been found to be advantageous to rotate the panels to allow the distal edges 40 of the inwardly extending elements 45 to hang downwardly during this step rather than to support the entirety of the individual panels as they are aligned.) The idlers 112 and 113 are preferably configured such that the pathlength of first panel 310 is different from that of third panel 330 and the pathlength of second panel 320 is different from that of fourth panel 340. This aligns the pairs of panels (310, 330) and (320, 340) in the machine direction such that they may be brought together in the proper configuration to form the multi-directional side panels 30, as are shown in FIG. 4.

Once the pairs of panels (first panel 310 and third panel 330) and (second panel 320 and fourth panel 340) have been aligned, the panels are preferably rotated such that they are in a horizontal configuration (i.e. the distal edges 40 are no longer hanging downwardly). The pairs of panels (310, 330) and (320, 240) are then positioned via idlers 114 and 115 such that the pairs overlay one another as shown in FIGS. 3 and 4. At this point in the process at least a portion of the distal edges 40 of pairs of panels (310, 330) and (320, 340) are in an overlapping configuration. In a particularly preferred embodiment, the panels are aligned such that the distal edges 40 of the panels are coincident with each other. As used herein, the term "coincident" means that a substantial portion, if not all of the distal edge of one panel overlaps a substantial portion, if not all of another panel. This configuration is illustrated by the side panels 30 in FIG. 4. (The arrows in FIG. 4 illustrate how portions of the panels 310, 320, 330 and 340 are configured so as to form the side panels 30.)

At least a portion of the distal edges 40 of the overlapping panels are joined together by the combination apparatus 116. As used herein, the term "joined" encompasses configurations where an element is directly secured to another element and configurations where an element is indirectly secured to another element by affixing one element to an intermediate member or members that are in turn affixed to the other element. The distal edges 40 of the overlapping panels may be joined continuously or intermittently by any means as are known in the art, including, but not limited to heat bonding, pressure bonding, adhesive bonding, dynamic mechanical bonding, ultrasonic bonding or any combination of these means. In a preferred embodiment, the distal edges 40 are joined with intermittent mechanical bonds. It is also preferred at this point in the process to join the longitudinal side edges 250 of the overlapping panels. However, embodiments are contemplated wherein the longitudinal side edges 250 are not joined together but, rather are joined to different parts or surfaces of the diaper web to which they are to be attached. For example, one longitudinal side edge may be joined to the topsheet while the other longitudinal side edge 250 is joined to the backsheet. Alternatively, the longitudinal side edges may be joined to opposing surfaces of the same component (e.g. topsheet or backsheet). (It should be noted that when edges are referred to as being joined herein, such as joining the distal edges 40 or joining the longitudinal side edges 250, it should be understood that material juxtaposed the edges may be joined along with the edges per se or in stead of the edges.) The resulting side panel web 400 is then metered into a cut/slip/bond unit. Any cut/slip/bond unit as is known in the art may be used, including, but not limited to the those units manufactured by Curt Joa Corporation of Sheboygan Falls, Wis.

Figure 12:
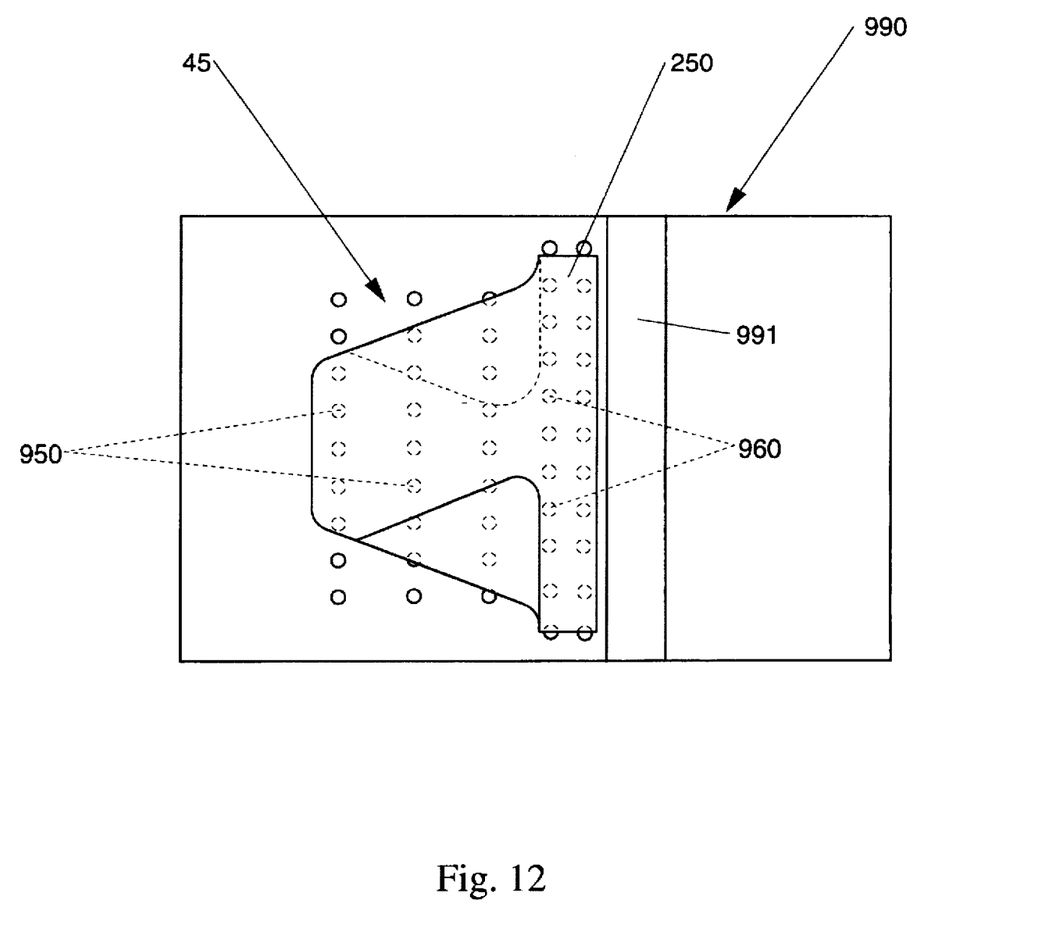
FIG. 12 is a schematic diagram of a portion of a preferred slip roll used in the process in the present invention.

The cut/slip/bond unit 118 first cuts the side panel web 400 into individual side panels 30 as shown in FIG. 4. This cut can be made by any cutting means as are known in the art. Once cut into side panels 30, the side panels 30 are positioned on a diaper web 120 and joined thereto. A standard industrial slip roll, such as manufactured by Curt Joa Corporation of Sheboygan Falls, Wis. may be used to position the side panels 30 on the diaper web 120. However, because of the irregular shape of the side panels 30, a slip roll capable of varying the amounts and location of vacuum is preferred. FIG. 12 shows a portion of a preferred slip roll comprising separately ported vacuum holes 950 and 960. The vacuum holes 950 hold the inwardly extending elements 45 in position on the slip roll 990 and are separately ported from the vacuum holes 960 that hold the longitudinal side edges 250 of the side panel web 400. (The separate porting of the vacuum holes 950 and 960 allows for the preferred variations in vacuum amounts and locations.) In a preferred embodiment, a low vacuum is applied to the longitudinal side edges 250 of the side panel web 400 while no vacuum is applied to the inwardly extending elements 45 before the side panel web 400 is cut into individual side panels 30. (Although a normal low vacuum is dependent on the materials and on the specific slip roll design, a suitable low vacuum would generally be between about 2 and about 15 inches of water column (WC) as read form a Magnahelic Vacuum gauge.) In one preferred embodiment, the longitudinal side edges 250 of the side panel web 400 are fed onto the slip roll 990 adjacent a curb 991 which helps hold the web 400 in a proper position for further processing. Once side panel web 400 has been cut and individual side panels 30 have been formed, a stronger vacuum, preferably between about 30 and about 60 inches WC, is applied to the entire side panel 30, including the longitudinal side edges 250 as well as the inwardly extending elements 45, as the side panel 30 is accelerated and positioned for placement on the diaper web 120. After the side panels 30 are properly positioned, the side panels 30 are joined to the diaper as web 120. The side panels 30 may be joined to any portion of the diaper web 120 including the topsheet, the backsheet or both. Further, as mentioned above, the longitudinal side edges 250 may be joined together and joined to the diaper web 120, or they may be joined to separate portions or surfaces of the diaper web 120 or the materials comprising the diaper web 120. Any of the above-described means for joining the side panels or any other means known in the art may be used to join the side panels 30 to the diaper web 120.

Alternative Embodiments

In one alternative embodiment, as the complementary panels (first panel 310 and second panel 320) and (third panel 330 and fourth panel 340) exit the die cutting assembly 110, they are separated as stated above. However, rather than directing the first panel 310 and third panel 330 to one assembly of idlers 112 and directing the second panel 320 and fourth panel 340 to another assembly of idlers 113, the complementary panels (310, 320) and (330, 340) are directed to the separate idler assemblies 112 and 113. The complementary panels (310, 320) and (330, 340) are then rotated phased and aligned as described above such that they may be brought together in the proper configuration to form an alternative embodiment of the multidirectional side panels 30 shown in FIG. 4. Once the complementary pairs (310, 320) and (330, 340) have been aligned, the process continues as described above with regard to the joining of the panels into a side panel web. Likewise, the cut/slip/bond operation, as described above, cuts individual side panels from the web, positions the side panels and bonds them to a diaper web.

Figure 5:
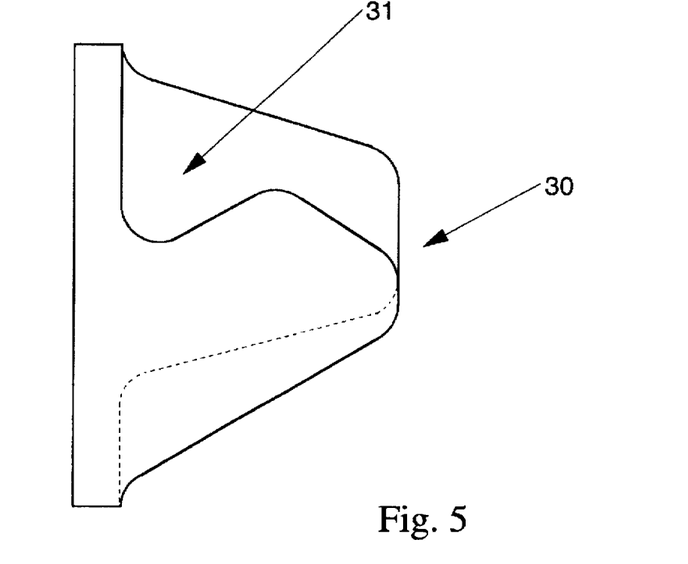
FIG. 5 is an illustration of an alternative embodiment of a multi-directional side panel manufactured by the process of the present invention.

In another alternative embodiment, as shown in FIG. 5, a portion of at least one of the panels comprised in the side panel 30 is "cut away". (As used herein, the term "cut away" refers to a portion of a web that has been removed by any means as are known in the art, including, but not limited to cutting, slitting, slicing, tearing, or perforating.) The cut away portion 31 provides an alternative means for imparting multi-directional stretch characteristics in the multi-piece side panel 30. The portion may be cut away at any point in the process. Further, the size and location of the cut away portion 31 of the side panel 30 can vary depending on the desired stretch characteristics of the side panel 30.

In yet another embodiment of the present invention, a single piece side panel 30, as shown in FIG. 6, is made with little or no wasted material. As used herein, the term "single piece" refers to side panels that, unlike the multi-piece multi-directional side panel 30 described above, comprise a single member that is cut, preferably activated, positioned and bonded to a diaper web. However, it should be noted that the term "single piece" does not exclude laminates or other multi-layer side panel members.

As shown in FIG. 7, the process for making single piece ear panels begins by providing a web of material 201 is to the apparatus 500 that forms the side panels 130. The material may be made on line or made off line and brought to the process. Suitable materials for the web include but are not limited to those described above with regard to the multi-piece side panels. The material 201 is preferably fed into the process through a tracking device 600 to center the material 201 before it enters the die cutting device 602. (In an especially preferred embodiment, the material is subjected to an activation process, as described above, to impart elasticity thereto before the material enters the die cutting device 602.) The die cutting device 602 severs the material 201 in a predetermined pattern 604. As above, the die cut pattern 604 is preferably continuous and preferably repeatedly cuts at least partially across the material 201 as the material 201 moves in the machine direction. In one preferred embodiment, as shown in FIG. 7, the die cut pattern continuously produces a series of alternating nested inwardly extending elements 605 defined by the cut 601 and terminating at a distal edge 606. The inwardly extending elements 605 extend inwardly from the longitudinal side edges 650 of the material 201. The die cut pattern 604 is preferably "regular" so as to produce a series of similarly shaped inwardly extending elements 605. (As used herein, the term "regular" refers to a pattern that is repeated so as to produce multiple members of generally the same size and shape. However, it should be noted that a regular pattern can include more than one size or shape so long as the multiple sizes or shapes are repeated.)

Once the material 201 has been die cut into complementary panels, first panel 700 and second panel 701, the panels 700 and 701 are preferably separated from each other. As shown in FIG. 7, this is done by idlers 610. In especially preferred embodiments, idlers 610 are in a vertical configuration so as to allow the inwardly extending elements 605 of the panels 700 and 701 to hang generally downwardly as they are positioned in both the machine direction and the cross machine direction. Each of the panels 700 and 701 preferably pass through a separate tracking device, tracking devices 612 and 614, respectively. The tracking devices 612 and 614 position the panels 700 and 701 such that they are in the proper machine direction and cross machine direction position and alignment to be joined with the diaper web 205. (Any suitable tracking device may be used to position the panels in the machine and cross machine direction. One such suitable tracking device is available from Russell T. Gillman, Inc., of Grafton, Wis. under the trade designation GILMAN SLIDE). In this embodiment, the panels 700 and 701 are properly aligned when the inwardly extending elements 605 of the first panel 700 are aligned with the inwardly extending elements 605 of the second panel 701 in the machine direction. The longitudinal side edges 650 of the panels 700 and 701 are also preferably aligned in the cross machine direction with the opposed longitudinal edges 204 of the diaper web 205 to which the side panels 130 will be joined. The inwardly extending elements 605 are shown in alignment in FIG. 7 just before the panels 700 and 701 pass into the cut/slip/bond unit 630.

After the panels 700 and 701 are aligned properly as described above, the panels 700 and 701 are preferably rotated by the transition guide 616 such that the inwardly extending elements 605 no longer hang generally downwardly. Rather, the rotation positions the inwardly extending elements 605 is outboard of the longitudinal side edges 650 of the panels 700 and 701. (As used herein, the term "outboard" means that the inwardly extending elements 605 have been rotated such that they are now extending in a direction away from the inwardly extending elements 605 of the complementary panel.) This rotation also ensures that the longitudinal side edges 650 of the panels 700 and 701 will be in a proper position to be joined with the longitudinal edges 204 of the diaper web 205. The transition guide may comprise any means as is known in the art for rotating web materials, including, but not limited to standard industrial plows.

Idler 618 moves the panels 700 and 701 from the transition guides 616 to the vacuum conveyor 620 which holds the panels 700 and 701 in position as they are fed into the cut/slip/bond unit 630. The vacuum conveyor may comprise any vacuum conveyor means known in the art. The cut/slip/ bond unit 630 cuts the panels 700 and 701 into individual side panels 130. The cuts are made at predetermined locations on the longitudinal side edges 650 between the inwardly extending elements 605. The individual side panels 130 are then spaced such that they are in a proper position to be joined with the diaper web 205 and then the side panels are joined to the diaper web 205. (In preferred embodiments, the material of the longitudinal side edges 650 between the inwardly extending elements 605 is also joined to the diaper web 205 to provide a stronger bond between the side panels 130 and the diaper web 205.) Any suitable cut/slip/bond unit may be used in this configuration including, but not limited to the cut/slip/bond unit described above with respect to the multi-piece side panel manufacturing process.

Figure 8:
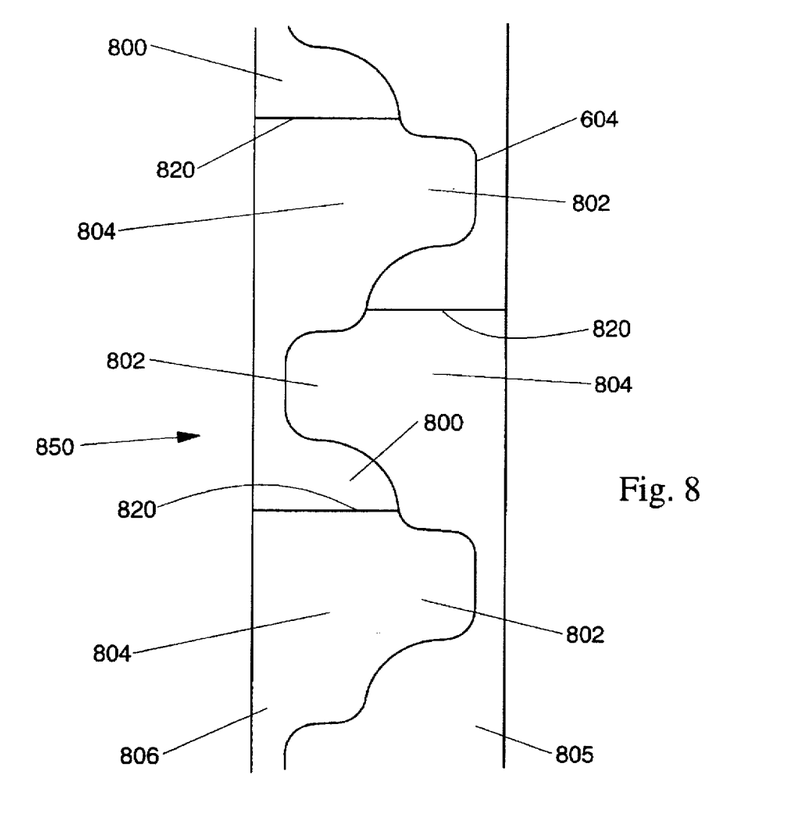
FIG. 8 is a plan view of a web of material showing one embodiment of the die cut pattern used in the process to manufacture side panels.
Figure 9:
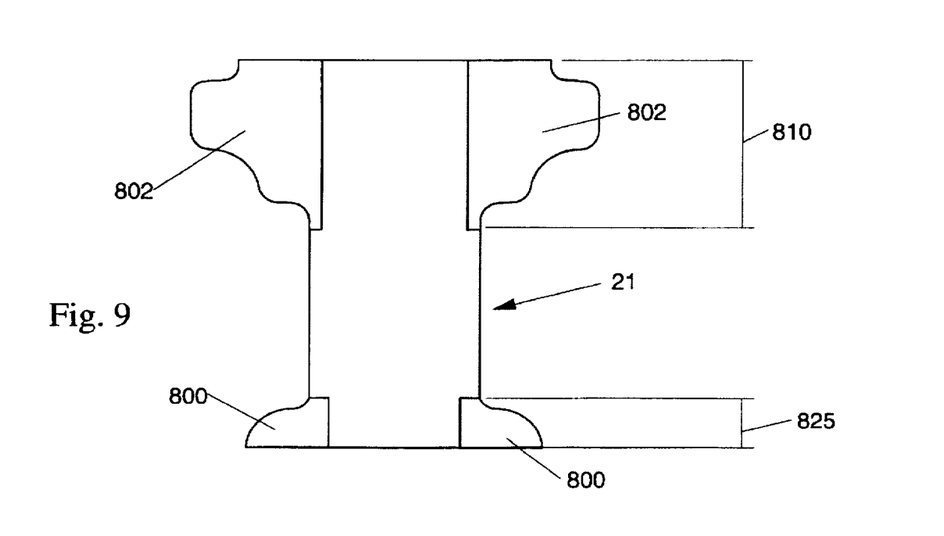
FIG. 9 is a plan view of an absorbent article comprising side panels manufactured in accordance with an alternative method of the present invention.

It is possible to use the above-described single piece process for manufacturing side panels to produce both front and rear side panels from a single continuous web with little or no wasted material. Varying the die cut pattern 604, to that shown in FIG. 8 or any comparable pattern provides for both front and rear side panels. The front side panels 800 and the rear side panels 802 are shown as they are cut from the web material 850 in FIG. 8 as well as on the diaper 21 illustrated in FIG. 9. The process for manufacturing both the front and rear side panels is the same as described above with regard to the single-piece side panels with an extra cut 820 being made to separate the inwardly extending elements 804 of the die cut panels, first panel 805 and second panel 806, into a front side panel 800 and a rear side panel 802. Once the front side panels 800 and the rear side panels 802 have been cut from the side panels 805 and 806, they are spaced by any means known in the art, including, but not limited to those previously described. The front side panels 800 are preferably positioned in the front waist region 825 of the diaper 21 while the rear side panels 802 are preferably positioned in the rear waist region 810 of the diaper 21. After being properly positioned, the side panels are joined to the diaper 21 by any means known in the art, including, but not limited to those means recited above.

Figure 10:
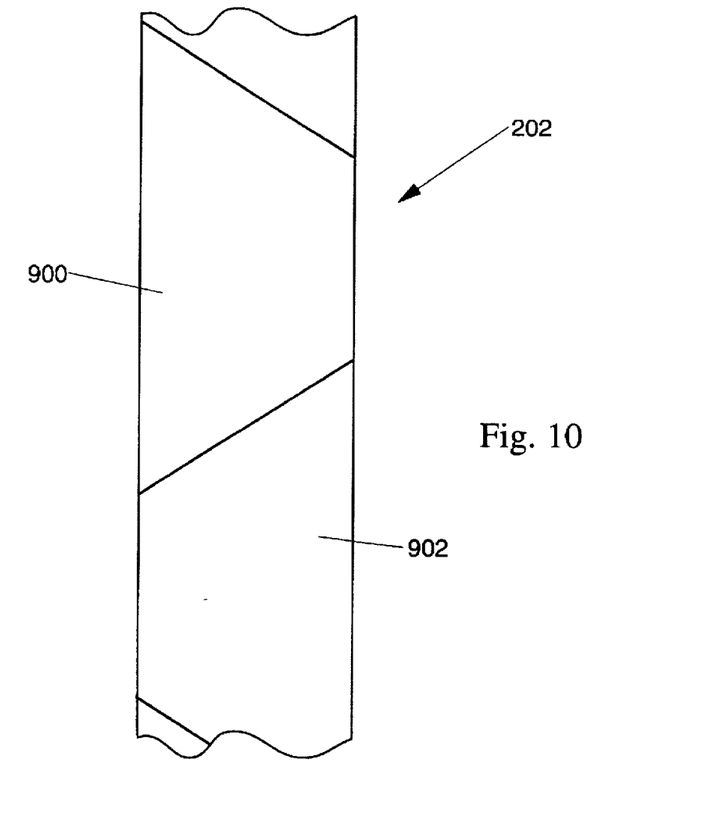
FIG. 10 is a plan view of a web of material showing an alternative embodiment of the die cut pattern used in the process of manufacturing side panels.
Figure 11:
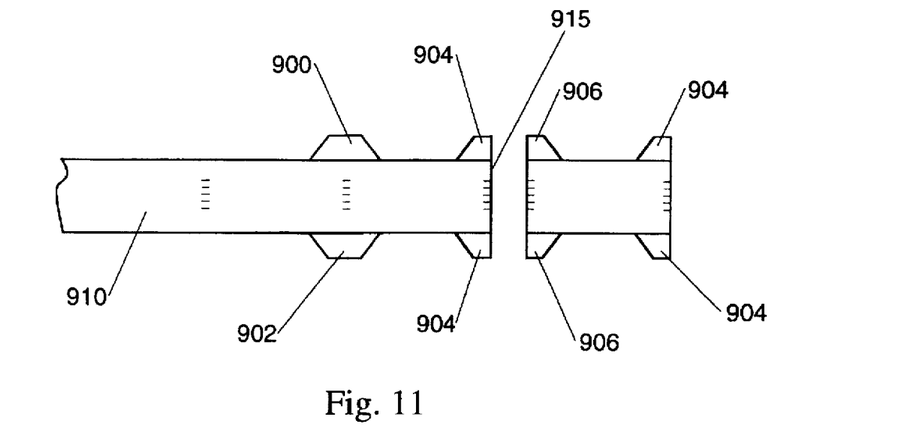
FIG. 11 is a plan view of the side panels and diaper made from the process described relating to FIG. 10.

FIGS. 10 and 11 show an alternative method of providing single-piece side panels for both the front and rear of a diaper. As above, a side panel web 202 is preferably die cut into panels 900 and 902. However, the panels 900 and 902 are then separated, aligned and joined with the diaper web 910 as shown in FIG. 11. After the panels are joined to the diaper web 910, the web and panels 900 and 902 are cut. The cut 915 separates the diaper web 910 into individual diapers and severs the panels 900 and 902 into front side panels 904 and rear side panels 906. Although all of the side panels in FIG. 10 are generally similar in size, it is possible to vary the size and shape of the front and rear side panels as desired to meet the particular needs of the absorbent article. The means for cutting, positioning and bonding the panels 900 and 902 to the diaper web 910 can be any suitable means including, but not limited to those means described in detail above.

While particular embodiments of the present invention have been illustrated and described, it would be obvious to those skilled in the art that various other changes and modifications could be made without departing from the spirit and scope of the invention. It is therefore intended to cover in the appended claims all such changes and modifications that are within the scope of this invention.

What is claimed is:

1. A zero scrap method for manufacturing multi-directional extensible side panels for an absorbent article, the method comprising the steps of:
   a) providing a web of material in a machine direction, said web having predetermined portions;
   b) activating said predetermined portions;
   c) making a continuous cut to sever said web into a first panel and a second panel, each of said panels having alternating, nested inwardly extending elements defined by said cut and terminating at a distal edge, said inwardly extending elements being offset in said machine direction;
   d) separating said first panel from said second panel;
   e) aligning said inwardly extending elements of said first panel and said second panel such that said distal edges of said inwardly extending elements are at least partially overlapping;
   f) joining at least a portion of said distal edge of said inwardly extending elements of said first panel with said distal edge of said inwardly extending elements of said second panel; and
   g) severing said first and said second panels at predetermined locations to create a side panel wherein said side panel is positioned adjacent one side of an absorbent article web before being joined to said absorbent article web.

2. The method of claim 1 further comprising the step of cutting and removing at least a portion of said first or second panels.

3. A zero scrap method for manufacturing multi-directional extensible side panels for an absorbent article, the method comprising the steps of:
   a) providing a web of material in a machine direction, said web having predetermined portions;
   b) cutting said web into, a first web portion and a second web portion;
   c) separating said first web portion and said second web portion;
   d) activating said first web portion and said second web portion;
   e) making a continuous cut to sever each of said web portions into a pair of panels, said first web portion comprising a first panel and a second panel, said second web portion comprising a third panel and a fourth panel, each pair of said panels having alternating, nested inwardly extending elements defined by said continuous cut and terminating at a distal edge, said inwardly extending elements being offset in said machine direction;
   f) separating said first panel from said second panel and said third panel from said fourth panel;
   g) aligning said inwardly extending elements of said first panel and said second panel such that said distal edges of said inwardly extending elements are at least partially overlapping;
   h) aligning said inwardly extending elements of said third panel and said fourth panel such that said distal edges of said inwardly extending elements are at least partially overlapping;
   i) joining at least a portion of said distal edge of said first panel with said distal edge of said inwardly extending elements of said second panel and said distal edge of said inwardly extending elements of said third panel with said distal edge of said inwardly extending elements of said fourth panel; and
   j) severing said first and said second panels and said third and said fourth panels at predetermined locations to create a first side panel and a second side panels, wherein said first side panel is positioned adjacent first side of an absorbent article web and said second side panel is positioned adjacent a second side of said absorbent article web opposite said first side panel before being joined to said absorbent article web.

4. The method of claim 3 wherein the step of activating said predetermined portions precedes the step (b) of cutting said web into two separate web portions.

5. The method of claim 4 further comprising the step of cutting and removing at least a portion of said first, second, third or fourth panels.

6. A zero scrap method for manufacturing multi-directional extensible side panels for an absorbent article, the method comprising the steps of:
   a) providing a web of material in a machine direction, said web having predetermined portions;
   b) cutting said web into, a first web portion and a second web portion;
   c) separating said first web portion and said second web portion;
   d) activating said first web portion and said second web portion;
   e) making a continuous cut to sever each of said web portions into a pair of panels, said first web portion comprising a first panel and a second panel, said second web portion comprising a third panel and a fourth panel, each pair of said panels having alternating, nested inwardly extending elements defined by said continuous cut and terminating at a distal edge, said inwardly extending elements being offset in said machine direction;
   f) separating said first panel from said second panel and said third panel from said fourth panel;
   g) aligning said inwardly extending elements of said first panel and said third panel such that said distal edges of said inwardly extending elements are at least partially overlapping;
   h) aligning said inwardly extending elements of said second panel and said fourth panel such that said distal edges of said inwardly extending elements are at least partially overlapping;
   i) joining at least a portion of said distal edge of said inwardly extending elements of said first panel with said distal edge of said inwardly extending elements of said third panel and said distal edge of said inwardly extending elements of said second panel with said distal edge of said inwardly extending elements of said fourth panel; and
   j) severing said first and said third panels and said second and said fourth panels at predetermined locations to create a first side panel and a second side panels, wherein said first side panel is positioned adjacent a first side of an absorbent article web and said second side panel is positioned adjacent a second side of said absorbent article web opposite said first side panel, before being joined to said absorbent article web.

7. The method of claim 6 further comprising the step of cutting and removing at least a portion of said first, second, third or fourth panels.

8. The method of claim 7 wherein the step of activating said predetermined portions precedes the step (b) of cutting said web into two separate web portions.

9. A method for manufacturing a combined, multi-piece, stretchable eared product for use in an absorbent article, said method comprising the steps of:
   a) providing a web of material under tension;
   b) continuously metering said web in a machine direction at a constant speed;
   c) slitting said web longitudinally to provide a first web and a second web having equal widths;
   d) activating said first and said second webs to impart an elastic-like characteristic to said webs;
   e) die cutting said first and said second webs into first, second, third and fourth patterned ear piece webs such that there is no excess trim, each of said patterned ear piece webs including a continuous portion and a plurality of ear portions;
   f) metering a first pair of said patterned ear piece webs such that said first pair of ear piece webs is oriented in a horizontal plane above a second pair of ear pieces webs;
   g) rotating said ear piece webs such that said ear piece webs are oriented vertically, wherein said plurality of ear portions hang down below said continuous portion;
   h) positioning said ear piece webs such that said webs comprising said first pair of webs overlap and said webs comprising said second pair of webs overlap;
   i) rotating said first pair of webs such that said first pair of webs is oriented horizontally;
   j) metering said first pair of webs in the same horizontal plane as said second pair of webs;
   k) bonding said first pair of webs and said second pair of webs to provide two distinct composite ear piece webs;
   l) attaching said first pair of ear piece webs and said second pair of ear piece webs to opposite sides of a central chassis; and
   m) successively cutting said combined multiple eared product web in the transverse direction at predetermined intervals to form discrete multiple eared products.

10. The method of claim 9 wherein the step of activating said predetermined portions precedes the step (b) of slitting said web.

11. The method of claim 9 wherein said first web and said second web are separated and spaced apart in a horizontal plane prior to being activated.

12. The method of claim 9 wherein said elastic-like characteristic imparted to said webs is in the direction of elongation.

13. The method of claim 9 wherein said first pair of patterned ear piece webs comprises said first and third ear piece webs and said second pair of patterned ear piece webs comprises said second and fourth ear pieces webs.

14. The method of claim 9 wherein said activating said first and said second webs imparts an activating pattern phased in both machine direction and cross direction to the die cut patterns.

15. The method of claim 9 wherein said first and said second pairs of webs are mechanically bonded to provide said two distinct composite ear piece webs.

16. The method of claim 9 wherein said first and said second pairs of webs are adhesively bonded to provide said two distinct composite ear piece webs.

* * * * *

UNITED STATES PATENT AND TRADEMARK OFFICE
CERTIFICATE OF CORRECTION

PATENT NO. : 5,705,013
DATED : January 6, 1998
INVENTOR(S) : Michael G. Nease et al.

It is certified that error appears in the above-identified patent and that said Letters Patent is hereby corrected as shown below:

Column 4,
Line 12, "fills" should read -- films --.

Column 6,
Line 9, "mounts" should read -- amounts --.

Signed and Sealed this

Twenty-fifth Day of December, 2001

Attest:

JAMES E. ROGAN
Attesting Officer     Director of the United States Patent and Trademark Office